United States Patent

Schwarz et al.

[11] Patent Number: 5,705,495
[45] Date of Patent: Jan. 6, 1998

[54] SULFAMATE DERIVATIVES OF 1,3,5(10)-ESTRATRIENE DERIVATIVES, METHODS FOR THEIR PRODUCTION AND PHARMACEUTICALS CONTAINING THESE COMPOUNDS

[75] Inventors: Sigfrid Schwarz, Jena; Walter Elger, Berlin; Gudrun Reddersen; Birgitt Schneider, both of Jena; Ina Thieme, Graitschen; Margit Richter, Jena, all of Germany

[73] Assignee: Jenapharm GmbH & Co. KG., Jena, Germany

[21] Appl. No.: 732,742

[22] Filed: Oct. 18, 1996

Related U.S. Application Data

[60] Provisional application No. 60/017,160, Jan. 5, 1996.

[30] Foreign Application Priority Data

Oct. 19, 1995 [DE] Germany ............ 195 40 233.2

[51] Int. Cl.[6] .......... A61K 31/56; A61K 31/58; C07J 1/00; C07J 53/00
[52] U.S. Cl. .......... 514/182; 514/176; 540/113; 552/510; 552/548; 552/552; 552/558; 552/614; 552/617; 552/618; 552/624; 552/626
[58] Field of Search .......... 552/510, 548, 552/552, 558, 614, 617, 618, 624, 626; 514/176, 182; 540/113

[56] References Cited

U.S. PATENT DOCUMENTS

| | | | |
|---|---|---|---|
| 5,556,847 | 9/1996 | Johnson et al. | 514/178 |
| 5,604,215 | 2/1997 | Reed et al. | 552/626 |
| 5,616,574 | 4/1997 | Reed et al. | 552/626 |

*Primary Examiner*—Allen J. Robinson
*Assistant Examiner*—Barbara Badio
*Attorney, Agent, or Firm*—Webb Ziesenheim Bruening Logsdon Orkin & Hanson, P.C.

[57] ABSTRACT

The invention relates to new sulfamate derivatives of 1,3,5 (10)-estratriene derivatives of the general formula I

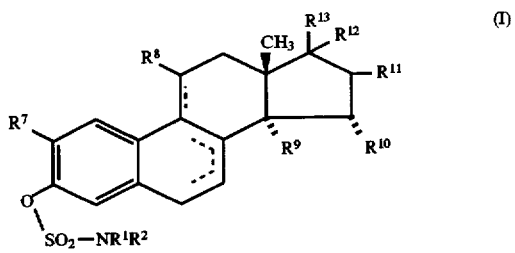

wherein the 3-sulfamate moiety is acylated, sulfonated or amidosulfonated. Furthermore, methods for the production of the compound and pharmaceutical preparations containing this compound are described. The compounds according to the invention have an estrogenic effect.

3 Claims, No Drawings

SULFAMATE DERIVATIVES OF 1,3,5(10)-ESTRATRIENE DERIVATIVES, METHODS FOR THEIR PRODUCTION AND PHARMACEUTICALS CONTAINING THESE COMPOUNDS

CROSS REFERENCE TO RELATED APPLICATION

This application claims the benefit of copending Provisional application Ser. No. 60/017,160, filed on Jan. 5, 1996.

This invention relates to new sulfamate derivatives of 1,3,5 (10)-estratriene derivatives, methods for their production, and pharmaceuticals containing these compounds.

Estrogens play a major role in hormonal contraception, in menopausal hormone replacement therapy (HRT), and for treating gynecologic diseases (e.g. mammary carcinoma) and andrologic diseases (e.g. prostatic carcinoma). For HRT and contraception, estrogens are mainly used together with a gestagen, e.g. levonorgestrel, desogestrel, norethisterone, cyproterone acetate, chlormadinone acetate, dienogest.

When used for contraception, estrogens are needed for safely suppressing follicle maturation and ovulation, but in addition they replace the endogenous ovarian secretion of estradiol which is suppressed to a major extent. This replacement is important for maintaining an artificial menstrual cycle and other genital functions, which could not be done to any satisfactory extent by just using a gestagen. In addition, endogenous and exogenous estrogens fulfil important central nervous and metabolic functions in the female organism: normal estrogen levels make a decisive contribution to a woman's well-being. Their presence in the system counteracts the development of cardiovascular diseases through various mechanisms: generation of "favourable" lipoprotein patterns in the blood, inhibition of lipid deposits in the walls of blood vessels, reduction in blood pressure by favourably influencing the vascular tonus, lowering of the perfusion resistance in essential vascular sectors, attenuation of contractile stimuli at the vascular muscle. The tunicae intimatae, when influenced by estrogens, release factors that counteract the formation of thrombi. Estrogens are indispensable for preserving the bone structure in women. If they are gone, this may result in destruction of the bone (osteoporosis). These latter "central nervous" and "metabolic" effects of estrogens are a main aspect of HRT. It can be considered a proven fact that estrogens have analogous functions in the male organism, and that their withdrawal results in similar disorders as in women. The only difference between the two sexes is that hormone production in males ceases less regularly and at a later age than that in women.

But notwithstanding all positive aspects of estrogen therapy there are unsolved problems, too, which restrict the therapeutic use of estrogens or entail undesired effects:

The known estrogens show pharmacokinetic deficits. Natural estrogens (estradiol, estrone, estrone sulfate, esters of estradiol, estriol) become bioavailable only to a very low degree when taken orally. This degree may vary so much from person to person that general dosage recommendations cannot be given. Fast elimination of the substances from the blood is another problem. Estrogen replacement under HRT often has to be adjusted to the individual.

The same is true of synthetic estrogens. The most important synthetically altered estrogenic steroid is ethinyl estradiol (EE). This estrogen is dominant in oral hormonal contraception. Apart from EE, mestranol is used in a few cases; this is a "prodrug" that is metabolized to EE in the organism. When applied orally to humans, EE has a much better bioavailability than the natural estrogens mentioned above, but its oral bioavailability varies to an extraordinary extent from individual to individual. Several authors have pointed to this as well as to the fact that concentrations in the blood proved to be highly irregular after oral application of this substance (Goldzieher, J. W. 1989, Goldzieher, J. W. 1990, Hümpel, M. 1987, Kuhnz, 1993).

In addition, the known estrogens show pharmacodynamic deficits. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. The secretion activity that is controlled by estrogens in the human liver includes synthesis of transfer proteins CBG, SHBG, TBG, angiotensinogen, several factors that are important for the physiology of blood clotting, and lipoproteins. If natural estrogens are introduced to the female organism while avoiding passage through the liver (e.g. by transdermal application), the liver functions mentioned remain virtually unchanged. Therapeutically equivalent doses of natural estrogens (see definition above), when applied orally, result in clear responses of hepatic parameters: increase of SHBG, CBG, angiotensinogen, HDL (high density lipoprotein). These hepatic effects of estrogen are clearly stronger when, instead of natural estrogens, equine estrogen formulations (so-called conjugated estrogens) are used (Campbell, S. et al., 1981). Ethinyl estradiol and DES have an even greater hepatic estrogenicity.

When referring to antigonadotropic properties, EE is about 4 to 18 times more estrogenic in the liver than orally applied natural estrogens are (Campbell, S. et al., 1981). This is a very unfavourable dissociation of properties.

These deficits are of considerable clinical significance when known natural and synthetic estrogens are to be applied.

A known complication that may occur after applying high doses of estrogen to males suffering from prostatic carcinoma is fatal thromboembolism. The potential of EE to produce side effects in the liver determines, though in a somewhat weakened form, the strategy of oral hormonal contraception. With a view to desired contraceptive effects and maintenance of the menstrual process on the one hand, and the need to take into account the considerable side effect potential on the other, controlling EE levels in the blood may be compared to a tightrope walk. It is quite possible that a large percentage of women cannot apply oral contraceptives because either menstrual bleeding abnormities or estrogen-related side effects exceed the tolerance threshold.

Hormone therapy based on natural hormones generally requires individual dose adjustment when today's techniques are used. Such treatment poses many imponderabilities; there is a clear risk of over- or underdosing.

It is therefore a problem of the present invention to provide new compounds that have an estrogenic effect and do not show the disadvantages described.

This problem is solved according to the invention by providing new sulfamate derivatives of the general formula I

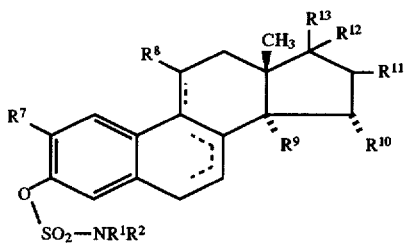

(I)

wherein $R^1$ is a —CO—$R^3$, —CO—$OR^4$, —CO—$NR^5R^6$, —$SO_2$—$R^4$ or —$SO_2$—$NR^5R^6$ group in which $R^3$ is a hydrogen atom or as defined in $R^4$, $R^4$ represents a $C_1$-$C_5$ alkyl residue, a $C_2$-$C_5$ alkenyl residue, a $C_3$-$C_6$ cycloalkyl residue or an aryl residue containing up to 9 carbon atoms, $R^5$ and $R^6$ are independent of each other and represent a hydrogen atom, a $C_1$-$C_5$ alkyl residue, an aryl residue containing up to 9 carbon atoms, or, together with the N atom, represent a polymethylene imino residue containing 3 to 6 carbon atoms, or a morpholino residue, $R^2$ is a hydrogen atom or a physiologically tolerable metal, or is as defined in $R^4$, $R^7$ and $R^8$ are independent of each other and represent a hydrogen atom, a hydroxy group or a $C_1$-$C_5$ alkoxy residue, $R^9$ and $R^{10}$ each represent a hydrogen atom, or together represent a methylene group, $R^{11}$, $R^{12}$ and $R^{13}$ are independent of each other and represent a hydrogen atom or a hydroxy group that may optionally be esterified with physiologically tolerable inorganic or organic acids, or $R^{12}$ or $R^{13}$ is an alkinyl residue containing up to 5 carbon atoms, rings B and C may optionally contain one or two double bonds, and $R^8$, $R^{11}$ and $R^{12}$ are independently placed either at the α- or β-position.

Physiologically tolerable metals that may be present in residue $R^2$ are, for example, alkaline or alkaline-earth metals. Sodium and potassium are particularly preferred.

Typical physiologically tolerable inorganic and organic acids with which the hydroxy groups of residues $R^{11}$, $R^{12}$ and $R^{13}$ may be esterified are, for example, phosphoric acid, sulfuric acid, oxalic acid, maleic acid, fumaric acid, lactic acid, tartaric acid, malic acid, citric acid, salicylic acid, adipic acid, and benzoic acid. Other acids that can be used are described, for example, in Fortschritte der Arzneimittelforschung, vol. 10, pp. 224–225, Birkhäuser Verlag, Basel and Stuttgart, 1966, and Journal of Pharmaceutical Sciences, vol. 66, pp. 1–5 (1977).

The compounds according to the invention have a greater systemic oral estrogenicity than ethinyl estradiol. They show a more favourable relation between desired and therapeutically undesired effects. When reaching their maximum estrogenic efficiency in the uterus or vagina, these substances are no more estrogenic in the liver than natural estrogens applied parenterally at an equipotent systemic dosage. Thus the new estrogenic compounds according to the invention are advantageous if compared with all other natural or synthetic estrogens known or used today.

It was found, surprisingly, that acylation, sulfonization or amidosulfonization of the 3-sulfamate group of 1,3,5(10) estratriene derivatives, other than alkylation, do not reduce but strengthen the systemic estrogenic effect. The low estrogenic effect of the compounds according to the invention on hepatic estrogen parameters if compared to their strong systemic activity is an additional advantage of the compounds according to the invention in comparison with the natural and synthetic estrogens used in oral therapy today.

The advantageous properties of the compounds according to the invention were proved using the following experimental methods on laboratory animals:

1. Induction of uterine growth and vaginal keratinization in ovariectomized rats after a single oral application (Allen-Doisy test): Test for quantifying systemic estrogenic activity.

2. Recording systemic and hepatic estrogenic effects in ovariectomized rats during and after a 7-day treatment: Test for determining the proportion of systemic and hepatic estrogenic activity.

The test substance or vehicle was administered once on day 1 (=d1) in the Allen-Doisy test. The observation and test period ended on day 4 (=d4). Vaginal cytology was checked daily until day 4. Uterine weights were determined at the end of the test.

In the test for systemic and hepatic estrogenic activity, the start of treatment was defined as day 1 (=d1), the end of treatment was day 7 (=d7). The animals were killed on day 8, and various inner organs (uteri, adrenal glands, liver) were taken out and weighed. Blood samples were taken under an ether narcosis from the retrobulbar plexus prior to treatment (=d0), and on d4 and d8. Angiotensin I, cholesterol, HDL and other factors were determined in the serum collected. Angiotensin I is a parameter for direct estrogenic effects in the liver, and the same is true of total cholesterol and HDL levels.

Methods of Determination

Angiotensin—modified RIA for renin activity, Sorin Co.; Cholesterol/HDL—enzymatic tests, photometric determination, reagents by Dr Bruno Lange GmbH.

Presentation of Findings

1. Systemic estrogenic activity:

Dosage at which a vaginal oestrus is induced;

2. Hepatic estrogenic activity:

Dosage at which uterine weights are doubled as compared to the ovariectomized control group, and dosages that cause a 50% increase or decrease of specific parameters as compared to control or previously obtained values.

Laboratory Animals

Adult female Wistar rats (breeder: Fa Tierzucht Sch önwalde GmbH) were ovariectomized. Treatment started two weeks after. The dosages given refer to the steroid portion of the esters. Assignment of the individual animals to the various groups was made at random.

The results of the animal experiments are presented in Tables 1 and 2:

1. Systemic estrogenic activity

Table 1 proves that acyl sulfamates of estrone and estradiol can trigger 100% vaginal keratinization at lower doses than their respective parent estrogens. These compounds even exceed the effect caused by ethinyl estradiol. The greater systemic activity of the acyl sulfamates also becomes apparent when comparing uterine growth under the influence of the estrogens tested. Table 1 shows that acyl sulfamates stimulate uterine growth to a greater extent than the reference estrogens tested along with them.

TABLE 1

| Substances | Test groups, number of animals[1] | | | | | |
|---|---|---|---|---|---|---|
| | Dosages (μg/animal, p.o.) | | | | | |
| | 0.1 | 1.0 | 10.0 | 100.0 | 300.0 | 1000.0 |
| E1 (estrone) | | | | 0/5 | 0/5 | 2/5 |
| E2 (estradiol) | | | | 0/5 | 5/5 | 5/5 |
| EE (ethinyl estradiol) | 0/7 | 3/7 | 2/7 | 7/7 | | |
| J 1045 | 0/5 | 0/5 | 5/5 | 5/5 | | |
| J 1046 | 0/5 | 0/5 | 3/5 | 5/5 | | |

[1] animals evaluated at the end of the tests

2. Hepatic estrogenic activity

Table 2 gives the dosages of the test substances that doubled uterine weights or resulted in a 50% change in blood concentrations of angiotensin-1 and HDL as compared to the control group. For ethinyl estradiol, the value thus defined of hepatic activity is below the dose that doubles uterine weights. This statement applies, in part, also to the natural estrogens tested. Acyl sulfamate estrogens show hepatic activity as defined only at dosages far higher than the doses that are efficient in utero.

TABLE 2

Relative uterine and hepatic estrogenic effect of J 1045

| sub-stance | Equipotent oral dose (μg/animal/day) | | | | |
|---|---|---|---|---|---|
| | uterus Δ 100% ↑ | angiotension I Δ 50% ↑ | HDL Δ 50% ↓ | quotient of A I Δ 50% ↑ and uterus Δ 100% ↑ | quotient of HDL Δ 50% ↓ and uterus Δ 100% ↑ |
| EE | 15 | 6.5 | 3 | 0.43 | 0.2 |
| E1 | 170 | 340 | 210 | 2 | 1 |
| E2 | 240 | 230 | 95 | 1 | 0.4 |
| J 1045 | 4 | >100 500 (extrapolated) | 15 | >25 125 (extra-polated) | 4 |

As Tables 1 and 2 show, the derivatives according to the invention of natural and synthetic estrogens have a considerably increased estrogenic effect as compared to their parent estrogens. In this way, therapeutic effects are achieved more easily, i.e. at lower doses, as would be achieved by oral application of the parent estrogens. A reduction of undesired metabolic effects results from the reduced hepatic estrogenic activity observed in relation to increased systemic activity.

Another object of the present invention is a method for the production of sulfamate derivatives of the general formula I

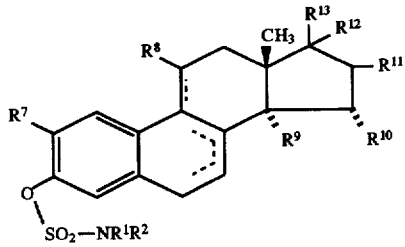

wherein the residues $R^1$ to $R^{13}$ are as defined above by reacting, in a generally known way, a) estra-1,3,5(10)-triene-3-yl sulfamate derivatives that carry at least one hydrogen atom at the nitrogen atom of their sulfamate residue, with an activated carboxylic acid, carbamic acid, sulfonic acid or amidosulfonic acid or b) 3-hydroxy-estra-1,3,5(10)-triene derivatives with an activated N-acyl amidosulfonic acid, N-sulfonyl amidosulfonic acid or N-amidosulfonyl amidosulfonic acid, optionally in the presence of a base, by further reacting the products obtained in a suitable way, and by optionally converting the products thus obtained into physiologically tolerable metal salts.

Another object of the present invention are pharmaceutical preparations containing at least one sulfamate derivative of the general formula I

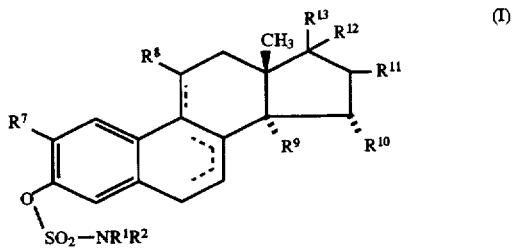

wherein the residues $R^1$ to $R^{13}$ are as defined above, optionally combined with pharmaceutically acceptable adjuvants and substrates.

An object of this invention are pharmaceutical preparations and medicines for oral, rectal, vaginal, subcutaneous, percutaneous, intravenous, or intramuscular application that contain a compound of the general formula I besides the common substrates and diluents.

The pharmaceuticals according to the invention are produced in a generally known way at an appropriate dosage depending on the intended application using the common solid or liquid substrates or diluents and adjuvants commonly used in pharmaceutical engineering. Preferred preparations are those forms suitable for oral administration, for example, tablets, film tablets, lozenges, capsules, pills, powder, solutions, suspensions, or depot forms.

Parenteral preparations such as injection solutions may also be produced, of course. In addition, suitable forms of application can be suppositories and forms for vaginal administration.

Tablets may be obtained, for example, by intermixing the active substance with known adjuvants, for example, inert diluents such as dextrose, sugar, sorbitol, mannite, polyvinylpyrrolidone, blasting agents such as maize starch or alginic acid, binders such as starch or gelatin, lubricants such as magnesium stearate or talcum and/or materials by which to produce a depot effect such as carboxyl polymethylene, carboxymethyl cellulose, cellulose acetate phthalate or polyvinyl acetate. Tablets may consist of several layers.

Lozenges may be produced accordingly by coating cores manufactured in analogy to tablet manufacture using agents generally applied to lozenge coating, for example, polyvinylpyrrolidone or shellac, Arabic gum, talcum, titanium dioxide, or sugar. The coating of the lozenge may also consist of several layers in which the adjuvants mentioned in the paragraph on tablets can be used.

Solutions or suspensions containing the agent according to the invention may, in addition, contain flavour-enhancing agents such as saccharin, cyclamate or sugar as well as, for example, aromatic substances such as vanillin or orange extract. Furthermore, they may contain suspending adjuvants such as sodium carboxymethyl cellulose or preserving agents such as p-hydroxybenzoates. Capsules containing active ingredients may be produced, for example, by mixing the active substance with an inert substrate such as lactose or sorbitol, and encapsulating such mixture in gelatin capsules.

Suitable suppositories can be produced, for example, by intermixing the active ingredients with appropriate substrates such as neutral fats or polyethylene glycol or their derivatives.

The invention will be explained in more detail using the following examples:

EXAMPLE 1

17-Oxo-estra-1,3,5(10)-triene-3-yl-(N-acetyl) Sulfamate (J 1046)

Estrone sulfamate (2.0 g) was dissolved in pyridine. Acetic anhydride (100 ml) was added to this solution, and the mixture was kept agitated for 2 hours at +23° C. It was then decomposed with ice, and the precipitate was filtered off, washed neutrally with water, and dried in an air flow. The title compound was obtained by recrystallizing from acetone.

Fp.: 218°–223° C. (acetone)

EXAMPLE 2

17β-Hydroxy-estra-1,3,5(10)-triene-3-yl-(N-butyryl) Sulfamate

Estrone sulfamate (1.3 g) was dissolved in a mixture of dichloromethane (45 ml) and triethyl amine (0.5 ml). p-Dimethylaminopyridine (0.455 g) and butyric acid anhydride (12 ml) were added under stirring at +23° C. After stirring for 20 hours at +23° C., the reaction solution was washed 5 times with water (70 ml each time), dried above anhydrous sodium sulfate, and evaporated in a rotary vacuum evaporator. The residue was mixed with n-hexane (50 ml) and started crystallizing. Some of the crystals filtered off (0.9 g) that represented 17-oxo-estra-1,3,5(10)-triene-3-yl-(N-butyryl) sulfamate were dissolved in a mixture of tetrahydrofurane (36 ml) and methanol (36 ml). Sodium hydridoborate (0.36 g) was added to the solution when it had cooled own to +5° C. When reduction was finished (DC check), the mixture was neutralized with acetic acid, and the product was precipitated with water. The title compound was obtained by recrystallizing from acetone/n-hexane.

Fp.: 197°–201° C. (acetone/n-hexane)

EXAMPLE 3

17-Oxo-estra-1,3,5(10)-triene-3-yl-(N-propionyl) Sulfamate

Triethyl amine (0.4 ml), p-dimethylaminopyridine (0.35 g) and propionic acid anhydride (7.4 ml) were added subsequently to a solution of estrone sulfamate (1.0 g) in dichloromethane (35 ml). The reaction mixture was stirred for 20 hours at +23° C., then it was decomposed with ice. The organic phase was washed with a saturated aqueous sodium hydrogencarbonate solution and water, dried above anhydrous sodium sulfate, and evaporated in a rotary vacuum evaporator, which yielded the title compound.

Fp.: 209°–211° C.

EXAMPLE 4

17-Oxo-estra-1,3,5(10)-triene-3-yl-(N-t-butoxycarbonyl) sulfamate

A solution of estrone sulfamate (2.0 g) in dichloromethane (70 ml) was esterified with butyloxylcarbonyl anhydride (2.5 g) in the presence of triethyl amine (0.8 ml) and p-dimethylaminopyridine (0.7 g) as described in Example 3. The reaction was finished after one hour at a temperature of +23° C. The product obtained after reprocessing was chromatographed on silica gel (eluents: dichloromethane/ethyl acetate; 7/3; v/v), and then recrystallized from acetone/n-hexane.

Fp.: 166°–169° C. (acetone/n-hexane)

EXAMPLE 5

17-Hydroxy-19-nor-17α-pregna-1,3,5(10)-triene-20-in-3-yl-(N-acetyl) Sulfamate 17-hydroxy-19-nor-17α-pregna-1,3,5(10)-triene-20-in-3-yl sulfamate (2.0 g) was dissolved in pyridine (50 ml). Acetic anhydride (50 ml) was added to the solution. The mixture was stirred for 2 hours at +23° C. The title compound was obtained after reprocessing according to Example 1; it was recrystallized from acetone.

Fp.: 218°–221° C. (acetone)

EXAMPLE 6

16α,17β-Dihydroxy-estra-1,3,5(10)-triene-3-yl-(N, N-dimethylcarbamoyl) Sulfamate 16α,17β-bis-(t-butyl-dimethyl)silyloxy-estra-1,3,5(10)-triene-3-ol (1.98 g) was dissolved in dichloromethane (50 ml) and triethyl amine (4.9 ml). The reaction mixture was stirred for 20 hours at +23° C. after adding p-dimethylaminopyridine (0.22 g) and dimethylcarbamoyl chloride (3.3 ml). The solution was then washed subsequently with dilute hydrochloric acid, water, saturated aqueous sodium hydrogencarbonate solution and water, dried above anhydrous sodium sulfate, and evaporated in a rotary vacuum evaporator. The residue was taken up in a mixture (75 ml) of acetic acid, water, and tetrahydrofurane (3/1/1; v/v/v). After allowing it to stand for 60 hours at +23° C., the mixture was neutralized with saturated aqueous sodium hydrogencarbonate solution and extracted with dichloromethane. The combined extracts were washed with water, dried above anhydrous sodium sulfate, and evaporated in a rotary vacuum evaporator. The title compound was obtained in the form of an amorphous white paste.

EXAMPLE 7

17-Oxo-estra-1,3,5(10)-triene-3-yl-[N-methyl-N-(N'-methyl)sulfamoyl]sulfamate

N-methylsulfamoyl chloride (3 ml) was added by dropping to a solution of estrone (3.0 g) in dichloromethane (1.2 l) and triethyl amine (28.5 ml). The mixture was kept agitated at +23° C. for 1.5 hours, then decomposed with water (200 ml); the organic phase was subsequently washed with dilute hydrochloric acid (1/1 v/v), water, saturated aqueous sodium hydrogencarbonate solution, and water, dried above anhydrous sodium sulfate and evaporated in a rotary vacuum evaporator. The crude product obtained was purified by chromatography on silica gel (eluents: toluene/chloroform/methanol; 80/15/5; v/v/v). The title compound was obtained after recrystallizing from acetone/n-hexane.

Fp.: 179°–185° C. (acetone/n-hexane)

EXAMPLE 8

17-Oxo-estra-1,3,5(10)-triene-3-yl-(N-t-butyl-N-t-butoxycarbonyl) Sulfamate

A solution of estrone sulfamate (2.0 g) in dichloromethane (70 ml) was esterified with butyloxylcarbonyl anhydride (2.5 g) in the presence of triethyl amine (0.8 ml) and p-dimethylaminopyridine (0.7 g) as described in Example 3. The reaction mixture was allowed to stand overnight at a temperature of +23° C. The product obtained after reprocessing was chromatographed on silica gel (eluents: dichloromethane/ethyl acetate; 7/3; v/v), and then recrystallized from acetone/n-hexane.

Fp.: 166°–169° C. (acetone/n-hexane)

EXAMPLE 9

17β-Hydroxy-estra-1,3,5(10)-triene-3-yl-(N-acetyl) Sulfamate (J 1045)

17-Oxo-estra-1,3,5(10)-triene-3-yl-(N-acetyl)sulfamat (1.0 g) produced according to Example 1 was reduced at 0° C. in a mixture of tetrahydrofurane (100 ml), methanol (100 ml), and sodium hydridoborate (0.68 g). After neutralizing the reaction mixture with acetic acid (2 ml), it was evaporated to dryness in a rotary vacuum evaporator. The residue was taken up in a mixture of water (150 ml) and ethyl acetate (150 ml). The organic phase was isolated, washed with water, dried with anhydrous sodium sulfate and evaporated in a rotary vacuum evaporator. The residue was recrystallized from acetone/n-hexane, which yielded the title compound.

Fp.: 198°–200° C. (acetone/n-hexane)

We claim:

1. Sulfamate derivatives of the general formula I

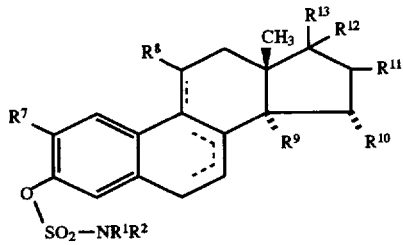

(I)

wherein $R^1$ is a —CO—$R^3$, —CO—O$R^4$, —CO—N$R^5R^6$, —SO$_2$—$R^4$ or —SO$_2$—NU$^5R^6$ group, in which $R^3$ is a hydrogen atom or is as defined in $R^4$, $R^4$ represents a $C_1$–$C_5$ alkyl residue, a $C_2$–$C_5$ alkenyl residue, a $C_3$–$C_6$ cycloalkyl residue or an aryl residue containing up to 9 carbon atoms, $R^5$ and $R^6$ are independent of each other and represent a hydrogen atom, a $C_1$–$C_5$ alkyl residue, an aryl residue containing up to 9 carbon atoms, or, together with the N atom, represent a polymethylene imino residue containing 3 to 6 carbon atoms, or a morpholino residue, $R^2$ is a hydrogen atom or a physiologically tolerable metal, or is as defined in $R^4$, $R^7$ and $R^8$ are independent of each other and represent a hydrogen atom, a hydroxy group or a $C_1$–$C_5$ alkoxy residue, $R^9$ and $R^{10}$ each represent a hydrogen atom, or together represent a methylene group, $R^{11}$, $R^{12}$ and $R^{13}$ are independent of each other and represent a hydrogen atom or a hydroxy group that may optionally be esterified with physiologically tolerable inorganic or organic acids, or $R^{12}$ or $R^{13}$ is an alkinyl residue containing up to 5 carbon atoms, rings B and C may optionally contain one or two double bonds, and $R^8$, $R^{11}$ and $R^{12}$ are independently placed either at the α- or β-position.

2. A method for the production of the sulfamate derivatives according to claim 1, comprising a) estra-1,3,5(10)-triene-3-yl sulfamate derivatives that carry at least one hydrogen atom at the nitrogen atom of their sulfamate residue, are reacted with an activated carboxylic acid, carbamic acid, sulfonic acid or amidosulfonic acid or b) 3-hydroxy-estra-1,3,5(10)-triene derivatives are reacted with an activated N-acyl amidosulfonic acid, N-sulfonyl amidosulfonic acid or N-amidosulfonyl amidosulfonic acid, optionally in the presence of a base.

3. A pharmaceutical preparation at least one sulfamate derivative according to claim 1 and a pharmaceutically acceptable adjuvants or substrates.

* * * * *

UNITED STATES PATENT AND TRADEMARK OFFICE
CERTIFICATE OF CORRECTION

PATENT NO. : 5,705,495
DATED : January 6, 1998
INVENTOR(S) : Sigfrid Schwarz et al.

It is certified that error appears in the above-identified patent and that said Letters Patent is hereby corrected as shown below:

Claim 1 Column 9 Line 40 "$NU^5R^6$" should read --$NR^5R^6$--.

Signed and Sealed this

Fifth Day of May, 1998

Attest:

BRUCE LEHMAN

Attesting Officer

Commissioner of Patents and Trademarks